(12) United States Patent
Girardeau et al.

(10) Patent No.: US 9,659,148 B2
(45) Date of Patent: **\*May 23, 2017**

(54) CAREGIVER ROUNDING COMMUNICATION SYSTEM

(71) Applicant: Hill-Rom Services, Inc., Batesville, IN (US)

(72) Inventors: David M. Girardeau, Pittsboro, NC (US); Kelly F. Walton, Cary, NC (US); Frederick Collin Davidson, Apex, NC (US); Kiana M. Dezelon, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/256,802

(22) Filed: Sep. 6, 2016

(65) Prior Publication Data
US 2017/0004264 A1    Jan. 5, 2017

Related U.S. Application Data

(63) Continuation of application No. 14/977,809, filed on Dec. 22, 2015, now Pat. No. 9,465,916, which is a
(Continued)

(51) Int. Cl.
*G06Q 50/22* (2012.01)
*G06F 19/00* (2011.01)
(Continued)

(52) U.S. Cl.
CPC ..... *G06F 19/327* (2013.01); *G06Q 10/063114* (2013.01); *G06Q 50/22* (2013.01); *G08B 25/10* (2013.01); *G06Q 30/018* (2013.01)

(58) Field of Classification Search
None
See application file for complete search history.

(56) References Cited

U.S. PATENT DOCUMENTS

| 5,760,704 A | 6/1998 | Barton et al. |
| 5,790,114 A | 8/1998 | Geaghan et al. |

(Continued)

FOREIGN PATENT DOCUMENTS

| WO | WO 97/25682 | 7/1997 |
| WO | WO 98/14888 | 4/1998 |

(Continued)

*Primary Examiner* — Brent Swarthout
(74) *Attorney, Agent, or Firm* — Barnes & Thornburg, LLP (57) ABSTRACT

An information technology system for a healthcare facility is provided. The system includes a first computer device to keep track of rounding intervals for caregivers and to determine whether the caregivers successfully complete their rounds in a timely manner for their assigned patients. The system also has a real time locating system (RTLS) that tracks locations of the plurality of caregivers and that is in communication with the first computer device. The system further has a number of graphical displays in communication with the first computer device. Each graphical display is operable to display a list of patients for whom rounds are due and to display reminder messages to the plurality of caregivers relating to rounding.

20 Claims, 6 Drawing Sheets

Related U.S. Application Data continuation of application No. 14/200,133, filed on Mar. 7, 2014, now Pat. No. 9,240,120.

(60) Provisional application No. 61/787,917, filed on Mar. 15, 2013.

(51) Int. Cl.
  *G08B 25/10* (2006.01)
  *G06Q 10/06* (2012.01)
  *G06Q 30/00* (2012.01)

(56) References Cited

U.S. PATENT DOCUMENTS

| | | | |
|---|---|---|---|
| 6,130,860 A | 10/2000 | Suzuki | |
| 6,288,978 B1 | 9/2001 | Suzuki | |
| 6,911,916 B1 | 6/2005 | Wang et al. | |
| 6,957,187 B1 | 10/2005 | Kameda | |
| 7,263,669 B2 | 8/2007 | Denholm | |
| 7,319,386 B2 | 1/2008 | Collins, Jr. et al. | |
| 7,344,079 B2 | 3/2008 | Steusloff et al. | |
| 7,364,067 B2 | 4/2008 | Steusloff et al. | |
| 7,475,019 B2 | 1/2009 | Rosenfeld et al. | |
| 7,522,477 B1 | 4/2009 | Sheldon | |
| 7,562,026 B2 | 7/2009 | DelMonego et al. | |
| 7,567,238 B2 | 7/2009 | Sugimoto et al. | |
| 7,587,329 B2 | 9/2009 | Thompson et al. | |
| 7,607,571 B2 | 10/2009 | Steusloff et al. | |
| 7,676,386 B2 | 3/2010 | Stephenson | |
| 7,746,218 B2 | 6/2010 | Collins, Jr. et al. | |
| 7,831,679 B2 | 11/2010 | Apacible et al. | |
| 7,904,312 B2 | 3/2011 | Denholm | |
| 8,027,849 B2 | 9/2011 | Johnson et al. | |
| 8,077,552 B1 | 12/2011 | Pope et al. | |
| 8,094,521 B2 | 1/2012 | Levy | |
| 8,169,304 B2 | 5/2012 | Schuman, Sr. et al. | |
| 8,224,683 B2 | 7/2012 | Manos | |
| 8,240,550 B2 | 8/2012 | Steusloff et al. | |
| 8,384,526 B2 | 2/2013 | Schuman, Sr. et al. | |
| 9,240,120 B2 * | 1/2016 | Girardeau | G08B 25/10 |
| 9,465,916 B2 * | 10/2016 | Girardeau | G06F 19/327 |
| 2006/0049936 A1 | 3/2006 | Collins, Jr. et al. | |
| 2006/0053035 A1 | 3/2006 | Eisenberg | |
| 2006/0149589 A1 | 7/2006 | Wager | |
| 2006/0173725 A1 | 8/2006 | Abraham et al. | |
| 2006/0247948 A1 | 11/2006 | Ellis et al. | |
| 2006/0267753 A1 | 11/2006 | Hussey et al. | |
| 2006/0277070 A1 | 12/2006 | Hungerford et al. | |
| 2007/0094046 A1 | 4/2007 | Cobbs et al. | |
| 2007/0112610 A1 | 5/2007 | Johnson et al. | |
| 2007/0122783 A1 | 5/2007 | Habashi | |
| 2007/0210917 A1 | 9/2007 | Collins, Jr. et al. | |
| 2007/0216660 A1 | 9/2007 | Sposato et al. | |
| 2008/0082363 A1 | 4/2008 | Habashi | |
| 2008/0106374 A1 | 5/2008 | Sharbaugh | |
| 2008/0164998 A1 | 7/2008 | Scherpbier et al. | |
| 2008/0281637 A1 | 11/2008 | Matz | |
| 2009/0021486 A1 | 1/2009 | Chaudhri et al. | |
| 2009/0043634 A1 | 2/2009 | Tisdale | |
| 2009/0089092 A1 | 4/2009 | Johnson et al. | |
| 2009/0089093 A1 | 4/2009 | Johnson et al. | |
| 2009/0094529 A1 | 4/2009 | Gonzalez et al. | |
| 2009/0112618 A1 | 4/2009 | Johnson et al. | |
| 2009/0119126 A1 | 5/2009 | Johnson et al. | |
| 2009/0125332 A1 | 5/2009 | Martin | |
| 2009/0125335 A1 | 5/2009 | Manetta et al. | |
| 2009/0125840 A1 | 5/2009 | Squilla et al. | |
| 2009/0178004 A1 | 7/2009 | Stoval, III et al. | |
| 2009/0182577 A1 | 7/2009 | Squilla et al. | |
| 2009/0212956 A1 | 8/2009 | Schuman et al. | |
| 2009/0254365 A1 | 10/2009 | Gravina | |
| 2010/0070294 A1 | 3/2010 | Horne et al. | |
| 2010/0079276 A1 | 4/2010 | Collins, Jr. et al. | |
| 2010/0191824 A1 | 7/2010 | Lindsay | |
| 2010/0198622 A1 | 8/2010 | Gajic et al. | |
| 2011/0205062 A1 | 8/2011 | Pesot et al. | |
| 2011/0208541 A1 | 8/2011 | Wilson et al. | |
| 2011/0276343 A1 | 11/2011 | Lagor et al. | |
| 2012/0010901 A1 | 1/2012 | Johnson et al. | |
| 2012/0029932 A1 | 2/2012 | Stein et al. | |
| 2012/0078661 A1 | 3/2012 | Sheldon et al. | |
| 2012/0089419 A1 | 4/2012 | Huster | |
| 2012/0253836 A1 | 10/2012 | Noble et al. | |
| 2012/0310664 A1 | 12/2012 | Long et al. | |
| 2014/0266642 A1 | 9/2014 | Girardeau et al. | |
| 2016/0110509 A1 | 4/2016 | Girardeau et al. | |

FOREIGN PATENT DOCUMENTS

| | | |
|---|---|---|
| WO | WO 2008/030249 | 3/2008 |
| WO | WO 2008/061833 | 5/2008 |
| WO | WO 2010/052624 | 5/2010 |
| WO | WO 2010/091073 | 8/2010 |

\* cited by examiner

CAREGIVER ROUNDING COMMUNICATION SYSTEM

CROSS REFERENCE TO RELATED APPLICATIONS

The present application is a continuation of U.S. application Ser. No. 14/977,809, filed Dec. 22, 2015, now U.S. Pat. No. 9,465,916, which is a continuation of U.S. application Ser. No. 14/200,133, filed Mar. 7, 2014, now U.S. Pat. No. 9,240,120, which claims the benefit, under 35 U.S.C. §119(e), of U.S. Provisional Application No. 61/787,917, which was filed Mar. 15, 2013, and each of which is hereby incorporated by reference herein in its entirety.

BACKGROUND

The present disclosure relates to systems for monitoring successful completion of tasks performed by caregivers in a healthcare facility, and particularly, to systems that monitor caregiver rounding. The present disclosure also relates to real time locating systems (RTLS's) used in healthcare facilities.

As part of normal procedures in healthcare facilities such as hospitals, caregivers are expected to make periodic patient rounds. According to this disclosure, a "round" is considered to be a visit to the patient's room by a caregiver to check on the patient. Some hospitals, for example, require rounding every two hours during the day and less frequently at night. Forgetting to round or having a low rounding frequency contributes to negative patient experiences in healthcare facilities, potentially resulting in lower Hospital Consumer Assessment of Healthcare Provider (HCAHP) scores. Accordingly, there is room for improvement in healthcare information technology systems from the standpoint of patient rounding.

SUMMARY

An apparatus, system, or method may comprise one or more of the features recited in the appended claims and/or the following features which, alone or in any combination, may comprise patentable subject matter:

An information technology system for a healthcare facility may include a first computer device that may keep track of rounding intervals for a plurality of caregivers and that may determine whether the caregivers successfully complete their rounds in a timely manner for their assigned patients. A successful round may be defined, for example, as one in which a caregiver visits an assigned patient within the rounding interval and remains in the patient's room for a threshold period of time.

The information technology system may further include a real time locating system (RTLS) that may track locations of the plurality of caregivers. The RTLS may include a plurality of badges each of which may be worn by a respective one of the plurality of caregivers and a plurality of receivers that may be located throughout the healthcare facility. Each of the receivers may be configured to receive wireless signals emitted from the badges of the caregivers within a reception range of each of the receivers. The RTLS may be in communication with the first computer device. The information technology system may further have a plurality of graphical displays that may be in communication with the first computer device. Each graphical display may be operable to display a list of patients for whom rounds are due and to display reminder messages to the plurality of caregivers relating to rounding.

According to some embodiments, the first computer device may determine automatically that the caregivers successfully complete each of their rounds based on information received from the RTLS indicating that the caregivers may be located within the patient rooms of the patients within the rounding intervals and for the threshold periods of time. The receivers of the RTLS may send messages to the first computer device and the first computer device may process the messages to determine the locations of the caregivers in the healthcare facility. For example, the RTLS may send messages to the first computer device via network infrastructure of the healthcare facility. In some embodiments, the RTLS may include an RTLS server which may receive messages from the receivers. The RTLS server may process the messages to determine the locations of the caregivers in the healthcare facility. The RTLS server may communicate location information to the first computer device.

In some embodiments, the first computer device may be included as part of a nurse call system. At least some of the plurality of graphical displays may be mounted in respective patient rooms and may serve as graphical room stations of the nurse call system. Alternatively or additionally, the plurality of graphical displays may be included as part of wireless communication devices that may be carried by the plurality of caregivers. The plurality of wireless communication device may be, for example, a tablet computer, a mobile telephone, and a smart phone.

Each graphical display of the plurality of graphical displays may be useable by each caregiver to view a list of patients assigned to the caregiver for rounding. Each graphical display of the plurality of graphical displays may be useable by each caregiver to indicate to the first computer device that the round is complete. Alternatively or additionally, each graphical display of the plurality of graphical displays may be useable by each caregiver to indicate to the first computer device that a task, other than rounding, is complete.

Further according to this disclosure, each graphical display of the plurality of graphical displays may be useable by each caregiver to re-prioritize tasks assigned to the caregiver. Each graphical display of the plurality of graphical displays may be useable by each caregiver to cancel an assigned task. Each graphical display of the plurality of graphical displays may show a rounding timer that may indicate how much time may be left within the rounding interval. In some embodiments, each graphical display of the plurality of graphical displays also may show a least one other timer that may relate to checking to see if an intravenous (IV) container needs replaced, checking to see if the patient needs pain medication, or checking to see if it is time to turn the patient onto one of the patient's left side and right side.

Further according to this disclosure, the graphical display also may show at least one icon that may be selected to place a call to a staff member. The staff member may include, for example, a registered nurse (RN), a certified nurse assistant (CNA), a transporter, or an environmental services person, just to name a few. Each graphical display of the plurality of graphical displays may be useable by caregivers to suspend at least one rounding task.

In some embodiments, the first computer device may be operable to change the rounding intervals. The first computer device may be operable to select an amount of time prior to expiration of the rounding intervals at which rounding reminder messages are sent to the plurality of graphical displays. Furthermore, the first computer device may be operable to change the threshold period of time.

According to some embodiments, the first computer device may be operable to generate a rounding compliance report. The rounding compliance report may include a table having blocks that indicate a successful round within the rounding interval, an unsuccessful round, and a suspended round. In some embodiments, an amount of time that the caregiver was located in each room may be shown in each block of the table for each successful round. The blocks may be colored a first color to indicate successful rounds, the blocks may be colored a second color to indicate unsuccessful rounds, and the blocks may be colored a third color to indicate suspended rounds. Alternatively or additionally, first icons may be shown in the blocks to indicate successful rounds, second icons may be shown in the blocks to indicate unsuccessful rounds, and third icons may be shown in the blocks to indicate suspended rounds.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
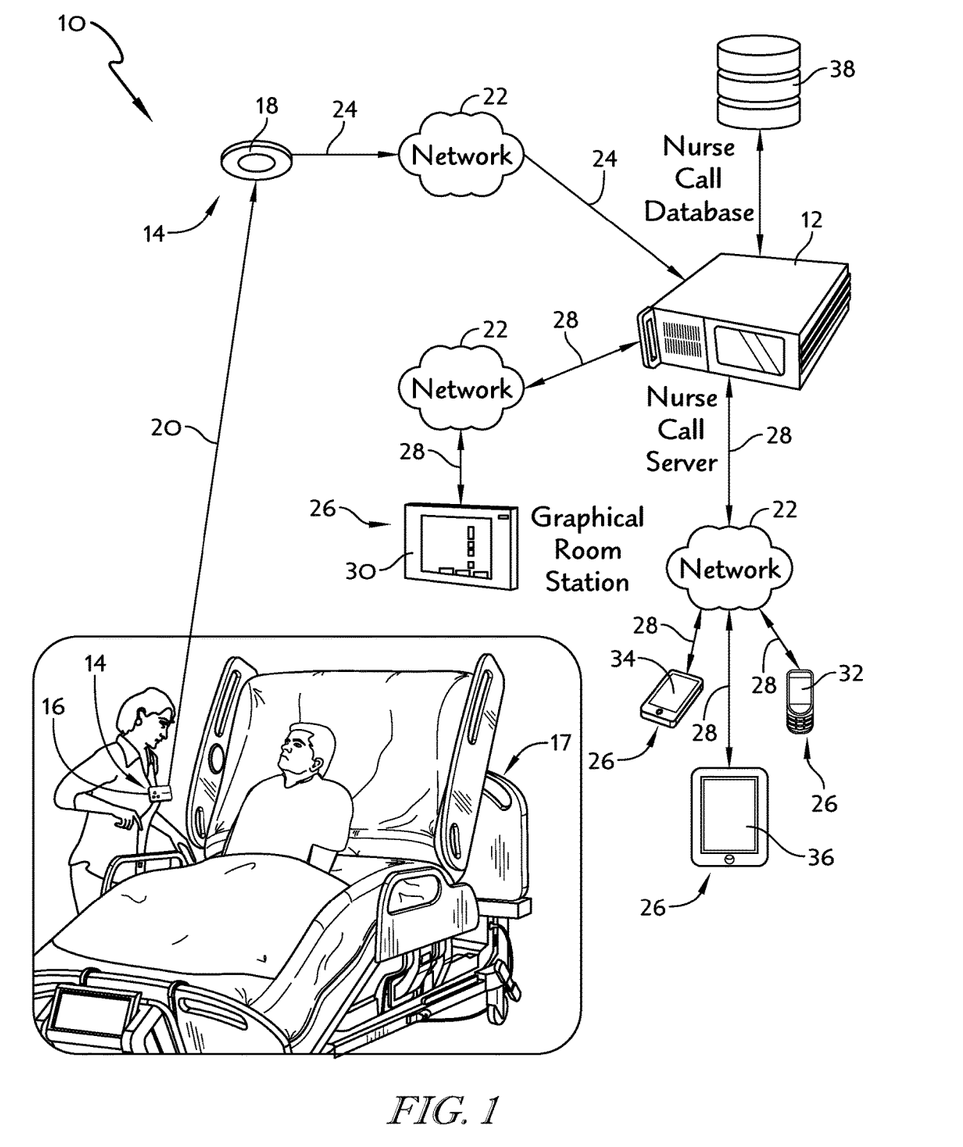
FIG. 1 is a block diagram of a healthcare information technology system showing a badge of real time locating system (RTLS) communicating with a receiver of the RTLS, the receiver communicating with a nurse call server which has a nurse call database, and the nurse call server communicating with a plurality of graphical displays including a graphical room station, a cellular telephone, a tablet computer, and a smart phone.

A healthcare information technology system 10 includes a first computer device 12, which in the illustrative example comprises a nurse call server, as shown in FIG. 1. Thus, first computer device 12 is sometimes referred to as server 12. A keyboard (not shown) and a monitor (not shown) are coupled to server 12 in some embodiments to provide inputs to server 12 and view information or outputs from server 12 as is well-known in the art. Alternatively, a touch screen display (not shown) associated with server 12 is used to provide inputs to server 12 and to view outputs from server 12 as is also well known in the art. Such keyboard/monitor arrangements or touch screen displays may be located at a master nurse call station, if desired.

System 10 includes a real time locating and tracking system (RTLS) 14 which includes a plurality of badges 16, each of which is worn by a respective caregiver, and a plurality of receivers 18 as shown diagrammatically in FIG. 1. Badges 16 are sometimes referred to in the art as "tags" and each of the terms badges and tags is intended to have the broad meanings of both according to this disclosure. Receivers 18 are located throughout the healthcare facility in which system 10 is installed and receive wireless signals from the badges 16 of various caregivers as indicated diagrammatically in FIG. 1 by arrow 20. For example, at least one receiver 18 is located in each patient room of the healthcare facility in some embodiments.

In some embodiments, an RTLS server (not shown) is included as part of system 14 and includes locating software that is used to process the packets of information transmitted to the RTLS server from receivers 18. However, in the illustrative example, nurse call server 12 includes the locating software such that server 12 receives the packets of information from receivers 18 for processing. Among the information included in the packets of information transmitted by each of the receivers 18 are a receiver identification (ID) and a badge ID of the badge(s) 14 in communication with the respective receiver 18. The location software correlates the badge ID with a particular caregiver to whom the badge 16 was issued and the location software correlates the receiver ID with a particular location in the healthcare facility. Thus, based on the packets of information sent by receivers 18, server 12 is able to determine which caregivers are at which locations within the healthcare facility.

As indicated diagrammatically in FIG. 1, receivers 18 communicate with server 12 via network infrastructure 22. Network infrastructure 22 is sometimes referred to herein simply as network 22. Arrows 24 indicate the one-way communication of packets of data from receivers 18 to server 12 via network 22. In FIG. 1, network 22 is shown diagrammatically and is intended to represent the components that interconnect server 12 with other computer devices of system 10 as well as representing the other computer devices themselves. Such components include, for example, wires, cables, routers, gateways, repeaters, additional servers, etc. Networks 22, of course, vary from healthcare facility to healthcare facility and thus, the construction and configuration of such networks 22 is at the discretion of the information technology personnel of any given healthcare facility.

System 10 further includes a plurality of graphical displays 26 that are each in bi-directional communication with server 12 via network 22 as indicated by doubled headed arrows 28 in FIG. 1. The examples of graphical displays 26 shown in FIG. 1 include a graphical room station 30, a cellular telephone 32, a smart phone 34, and a tablet computer 36. System 10 includes a multitude of graphical displays 26 and thus, it should be appreciated that, for example, stations 30 are included in each of the patient rooms, in some embodiments, and that many caregivers carry one or more of phones 32, 34 and tablet computers 36. Graphical room stations 30 are mounted at fixed locations in patient rooms, such as being mounted on a room wall, whereas phones 32, 34 and computer 36 are portable. Thus, arrows 28 in FIG. 1 represent both wired and wireless communication links of the devices with graphical displays to network 22 and to nurse call server 12. Phones 32, 34 and computer 36 are sometimes referred to herein as portable wireless communication devices 32, 34, 36 or just devices 32, 34, 36.

Server 12 includes a nurse call database 38 as shown diagrammatically in FIG. 1. Although database 38 is shown external to server 12 in FIG. 1, it will be appreciated that database 38 is internal to server 12 in some embodiments and comprises one or more memory devices, such as memory chips, a hard drive, or the like. Server 12 includes rounding software that tracks the whereabouts of caregivers within the facility based on information from RTLS 14. Database 38 stores the correlated badge ID, location ID, caregiver name, and location name in a table or array. Using the rounding software, server 12 determines whether each of the caregivers complete their assigned rounds in a timely manner. Protocols established by the healthcare facility determine the time intervals of how often a caregiver should check on each patient. According to some protocols, the time intervals may vary based on the time of day (e.g., one hour time intervals during the day and two hour time intervals at night) or based on the type of patient (e.g., one hour time intervals for a patient recovering from surgery and two hour time intervals for a labor and delivery patient).

In order for a round (i.e., a visit to a patient by a caregiver to check on the patient) to be considered a successful round, some hospital protocols establish a minimum amount of time that a caregiver needs to be present in the patient's room. Thus, threshold periods of time of two minutes or five minutes, for example, are not uncommon in this regard. The threshold periods may vary based on the time of day or type of patient. Based on the tracking of the locations of caregivers done by RTLS 14, the rounding software of server 12 is able to determine whether caregivers have been successful in making their rounds to assigned patients and to store the determinations in database 38 in connection with each of the established time periods.

Figure 2:
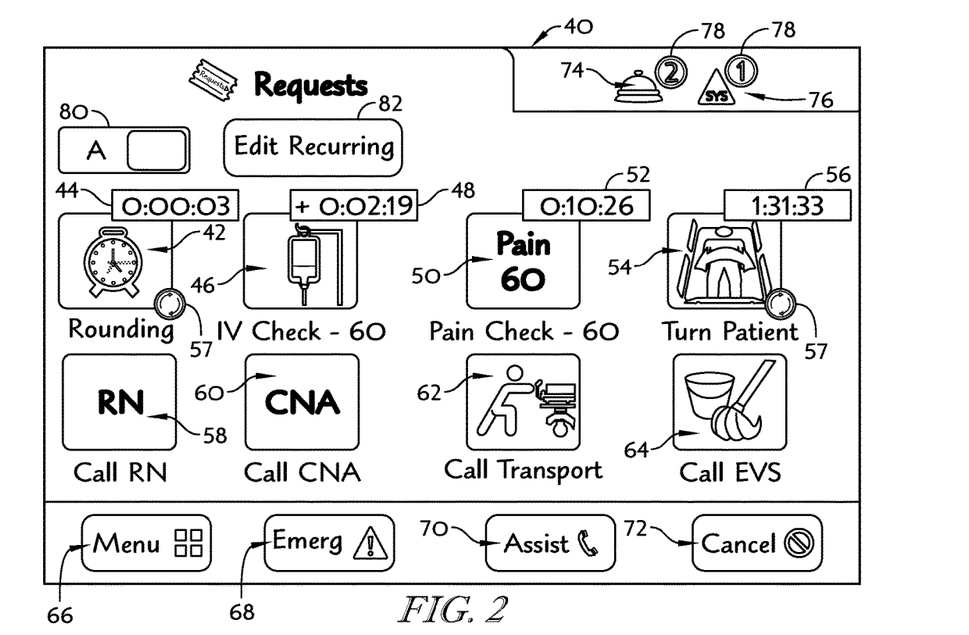
FIG. 2 is a screen shot of one of the graphical displays of the plurality of graphical displays showing times associated with icons related to Rounding, IV check, Pain Check, and Turn Patient.

Referring now to FIG. 2, an example of a screen shot of a rounding screen 40 that appears on graphical display 26 of station 26 and/or devices 32, 34, 36 includes a rounding icon 42 with a rounding timer 44 that overlaps a portion of the upper right corner of icon 42. The rounding timer 44 is a countdown timer indicating how much time is left within the rounding interval for a particular patient. In the illustrative example of screen 40 in FIG. 2, only three seconds are left in the rounding interval. Thus, the rounding interval is in the format hours (one digit): minutes (two digits): seconds (two digits) in the illustrative example.

Rounding screen 40 also includes an IV Check icon 46 with an IV Check timer 48 overlapping the upper right corner of icon 46, a Pain Check icon 50 with a Pain Check timer 52 overlapping the upper right corner of icon 50, and a Turn Patient icon 54 with a Turn Patient timer 56 overlapping the upper right corner of icon 54. In the illustrative example of screen 40 in FIG. 2, a plus sign (i.e., "+") is shown in front of the time (e.g. 0:02:19) on counter 48 to indicate the amount of time past the expiration of the time interval established for checking the amount of intravenous (IV) solution left in an IV bag or IV bottle. In some embodiments, a similar type of plus sign is used in connection with timers 52, 56. However, with regard to rounding timer 44, if a caregiver does not check on the patient within the rounding time interval, then such a situation is determined by the rounding software of server 12 to be an unsuccessful round and is logged as such in database 38. Timer 44 is then set back to the established time interval (e.g., 1:00:00, 2:00:00, or 3:00:00) and begins to count down anew for the next rounding time interval.

When screen 40 is displayed on the graphical displays 26 of room stations 30, it is clear as to which patient the information on screen 40 pertains. Namely, it is the patient in the same room in which station 30 is located, or if there are two patients in a semi-private room, it is the patient closest to the particular station 30 within the semi-private room. In some embodiments, database 38 correlates a station ID of each station 30 to a room location and optionally, to a patient associated with the room location. Thus, server 12 provides information to stations 30 that is specific to the corresponding patient at each location of stations 30. For example, some patients may not need to be turned in which case icon 54 and associated timer 56 are omitted from screen 40 in such situations. As another example, some patients may not be receiving IV fluids in which case icon 46 and associated timer 48 are omitted from screen 40 in such situations.

It is contemplated by some embodiments of this disclosure, that the rounding intervals are not patient specific, but rather, are unit specific in that each of the rounding intervals for each patient in a particular unit of a healthcare facility is the same and each patient has the same caregiver rounding protocol (e.g., every hour or every two hours). Accordingly, the timers 44 of rounding icons 42 display the same countdown time information for all patients of the associated unit in such embodiments. Optionally, icons 46, 50, 54 also may have associated time intervals that are established on a unit wide basis rather than being patient specific, if desired. In the illustrative example of FIG. 2, circular icons 57 with a pair of curved arrows slightly overlap the bottom right corners of icons 42, 54 to indicate that the rounding and turn patient tasks are recurring tasks that must be repeated within the established time intervals during a patient's stay. The absence of icons 57 at the bottom right corners of icons 46, 50 indicate that the IV check and pain check tasks are just one-time or non-recurring tasks.

When screen 40 is shown on one of the portable wireless communication devices 32, 34, 36, server 12 provides information to devices 32, 34, 36 to update screen 40 based on information from RTLS 14. Because the caregivers carrying devices 32, 34, 36 are also wearing badges 16, server 12 is able to determine which room each of the caregivers is located and provide the particular device 32, 34, 36 carried by the caregiver with the information from database 38 needed to populate screen 40 on the respective device 32, 34, 36. Alternatively or additionally, devices 32, 34, 36 are operable to display on the respective graphical display screens 26 a list of patients or room numbers which are selectable by a caregiver to retrieve the information on screen 40 for a particular patient or room selected.

It is contemplated by some embodiments of this disclosure that RTLS 14 is omitted. In such embodiments, the rounding timer 44 is started and reset manually on graphical room stations by caregivers via selection of icon 42. Thus, after a caregiver has visited a patient for a threshold period of time, the caregiver touches icon 42 on screen 40 of station 30 to restart the rounding timer countdown beginning at the full rounding time interval (e.g., one, two or three hours). When the patient is first admitted to the room, the caregiver touches icon 42 to start the first rounding interval. In some embodiments, including those in which RTLS 14 is present, an admission, discharge, and transfer (ADT) system is included in network 22 and when the patient is initially assigned a room at an ADT computer of the ADT system, the ADT computer sends a message to server 12 which, in turn, sends a message to room station 30 of the associated to room to start counting down time on timer 44 of icon 42 for the first rounding interval. This may occur even before the patient arrives at the room in some embodiments.

In other embodiments, the timer 44 starts to count down when the patient is sensed to be present in the room or on the bed. For example, if the patient is given a badge 16 to wear or is given a wristband that emits wireless signals to receivers 18, then the RTLS system determines when the patient reaches the room and communicates that information to server 12 which, in turn, sends a message to the corresponding room station 30 to start the countdown timer 44 of rounding icon 42. In some embodiments, a hospital bed 17 (FIG. 1) includes sensors, such as load cells of a weigh scale system or force resistive sensors on a mattress support deck, that sense the presence of the patient in bed 17 as is well known in the art. It is also well known in the art for bed 17 to send bed status data or information to nurse call server 12. Thus, based on signals from bed 17 server 12 is able to determine that the patient is on the bed and, in response, signals the associated station 30 to start countdown timer 44 of icon 42 on screen 40.

Still referring to FIG. 2, screen 40 includes a Call RN icon 58, a Call CNA icon 60, a Call Transport icon 62 and a Call EVS icon 64. Each icon 58, 60, 62, 64 is selectable to call a registered nurse, a certified nurse assistant, a patient transport, or an environmental services staff member, respectively. Thus, in the illustrative example, each of stations 30 and devices 32, 34, 36 have voice communication capability. In some embodiments, tablet computer 36 does not have voice communication capability in which case icons 58, 60, 62, 64 are omitted from screen 40.

In response to either of icons 58, 60 being selected, a call is placed via the network 22 to a specific person (e.g., the registered nurse or certified nurse assistant) assigned to the particular patient associated with the screen 40 that is being displayed on station 30 or devices 32, 34, 36 at the time when icon 58 or icon 60 was selected. In some embodiments, the call to a specific person (e.g., RN or CNA in the illustrative example) is made to a phone number of a device 32, 34, 36 carried by the specific person. In some embodiments, the call to the specific person is made to one of the graphical room stations 30 where the specific person is determined to be based on information from the RTLS. Thus, bidirectional voice communications are able to be established between one or more of devices 32, 34, 36 and stations 30, and vice versa in some embodiments. Accordingly, in some embodiments, database 38 stores information regarding which RN's and CNA's, or other types of caregivers, are assigned to each of the patients or room locations or both and display 26 shows an associated icon on screen 40 for use in contacting the assigned caregiver(s).

In some embodiments, in response to selection of either of icons 58, 60, a menu of call options, such as whether to call a number associated with the person's phone 32, 34 or whether to call the station 30 of a room in which the person is known to be located, is shown on the graphical display 26 for selection by the user. Additional discussion of the use of graphical room stations, like station 30, to contact specific caregivers via a menu of options is included in U.S. Pat. No. 8,169,304 and U.S. Patent Application Publication No. 2009/0212956 A1, both of which are hereby expressly incorporated by reference herein for all that they teach to the extent not inconsistent with the present disclosure which shall control as to any inconsistencies. In response to either of icons 62, 64 being selected, a call is placed via the network 22 to a central dispatch manager that manages the dispatch of either patient transporters or environmental services personnel, as the case may be, and then the manager decides, or uses software to decide, which particular staff member to dispatch based on availability of staff members.

In the illustrative example, screen 40 also has a Menu icon 66, an Emergency icon 68, an Assist icon 70, and a Cancel icon 72. Menu icon 66 is selected by the user to navigate to a main menu screen of station 30 or device 32, 34, 36. An example of menu screen is shown and described in U.S. Patent Application Publication No. 2011/0208541 A1 ("the '541 publication") which is hereby expressly incorporated by reference herein to the extent not inconsistent with the present disclosure which shall control as to any inconsistencies. See particularly, the discussion associated with FIG. 13 of the '541 publication.

Emergency icon 68 is selected in emergency situations to send simultaneously a call message to a designated response team of people. Assist icon 70 is also selected to send simultaneously a call message to a designated response team of people. The response teams are set up at the discretion of administrators of system 10 within healthcare facilities. It is typically the case that the response team associated with Assist icon 70 is smaller in number than the response team associated with Emergency icon 78. The devices to which the call messages are also configurable such that messages are able to be sent to designated room stations 30 or devices 32, 34, 36 at the option of the system administrator.

In some embodiments, selection of each of icons 68, 70 results in a dome light of the associated patient room being illuminated to indicate either an emergency condition (e.g., red light on dome light) or assist condition (e.g., yellow light on dome light). Details of suitable dome light assemblies can be found in U.S. Pat. No. 8,384,526 which is hereby expressly incorporated by reference herein to the extent not inconsistent with this disclosure which shall control as to any inconsistencies. Cancel icon 72 is selected to cancel any of the calls made using any one of icons 58, 60, 62, 64, 66, 68, 70.

Screen 40 also includes a pair of status summary icons including a call bell icon 74 and a system alert icon 76. Each of icons 74, 76 have a number icon 78 that indicates the number of active calls or system alerts that are occurring unit wide as monitored by the nurse call software of server 12. In the illustrative example, there are two pending nurse calls as indicated by icon 78 adjacent call bell icon 74 and there is one system alert as indicated by icon 78 adjacent system alert icon 76. Selection of either of icons 74, 76 brings up associated information about the calls or alerts on graphical display 26 of the associated station 30 or device 32, 34, 36. If there are no active calls or system alerts, then icons 74, 76 and the associated number icons 78 are not displayed on screen 40 of graphical display 26.

In the illustrative example, screen 40 has an A/B toggle box 80. Toggle box 80 permits the caregiver viewing screen 40 on graphical display 26, when located in a semi-private room having two patients on two different beds, to select whether information relating to patient A or patient B is shown on screen 40. Tapping icon 80 switches the information on screen 40 back and forth between patients A and B. In the illustrative example of FIG. 2, the letter A is visible on the left side of box 80 to indicate that the information on screen 40 pertains to patient A of the associated semi-private room and a small box within box 80 is situated on the right side of box 80 to cover the letter B. If box 80 is tapped when in the configuration shown in FIG. 2, the small box within box 80 moves to the left thereby exposing letter B and covering letter A. Box 80 is omitted from screen 40 if graphical display 26 is located in a private room having only one patient.

Figure 3:
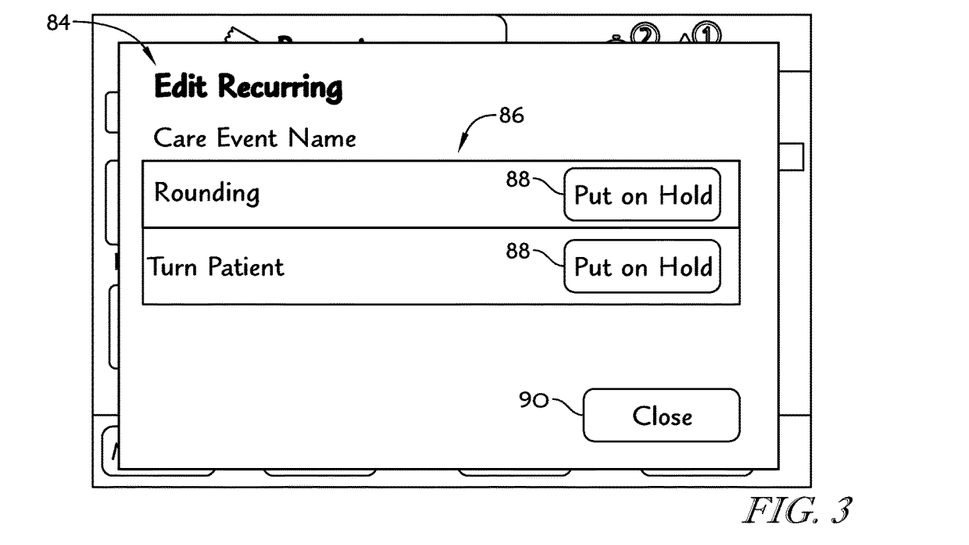
FIG. 3 is a screen shot of one of the graphical displays of the plurality of graphical displays showing the graphical display having Put on Hold buttons that are used to suspend a rounding task and a turn patient task.

Screen 40 also includes an Edit Recurring icon or button 82 as shown in FIG. 2. In response to button 82 being selected on screen 40, an Edit Recurring pop-up window 84 appears on graphical display 26 as shown in FIG. 3. Window 84 includes a menu 86 having a list of the recurring tasks that the caregiver is able to suspend by selection of a respective Put on Hold icon or button 88 which appears on the menu 86 to the right of each task name. In the illustrative example of FIG. 3, Rounding and Turn Patient task names are listed in menu 86 and are able to be suspended by selection of a respective icon 88. Window 84 also includes a Close icon or button 90 that is selected to close out of window 84 and return to screen 40.

A task is suspended by a caregiver using buttons 88 of window 84, for example, when a patient leaves the patient room for surgery or therapy or otherwise is going to be absent from the patient room for an extended period of time. When the patient returns back to the room, the caregiver selects rounding icon 42 and/or turn patient icon 56 on screen 40 to start the rounding and turn assist time intervals along with respective countdown timers 44, 56 once again in some embodiments. In other embodiments, countdown timers 44, 56 automatically restart when the patient is sensed to have returned back to the room or bed 17 using RTLS 14 or one or more sensors on bed 17 as described above.

When a patient is discharged from the healthcare facility, then the recurring tasks, such as rounding, IV check, pain check, and turn patient associated with icons 42, 46, 50, 54 in the illustrative example of screen 40, are no longer applicable for the discharged patient. If system 10 includes an ADT system, then discharge information is transmitted from the ADT system to server 12 which, in turn, automatically suspends or stops monitoring for successful completion of the tasks and zeroes out the respective timers 44, 48, 52, 56 on screen 40. If system 10 does not include an ADT system, then patient discharge information is either entered directly to server 12 using its associated input device (e.g., keyboard or touch screen) or a caregiver manually suspends each of the recurring tasks using buttons 88 in window 84 after selecting button 82 on screen 40 of station 30 in the room where the discharged patient was previously located.

According to this disclosure, server 12 generates reports relating to rounding compliance based on information in database 38 and information received from RTLS 14, stations 30 and devices 32, 34, 36. In some embodiments, these reports are accessible using various computer devices of network 22 and using station 30 and devices 32, 34, 36. In other embodiments, more limited access is given to the reports, such as being accessible only using the output device associated with server 12, for example. FIGS. 4-8 show a few examples of rounding compliance reports. There are a number of possible formats for conveying rounding compliance information and all such formats are intended to be within the scope of this disclosure. Such formats include, for example, pie charts, bar graphs, line graphs, and the like. However, in the illustrative examples, a tabular format with color coding and/or icons is used as will be described below.

Figure 4:
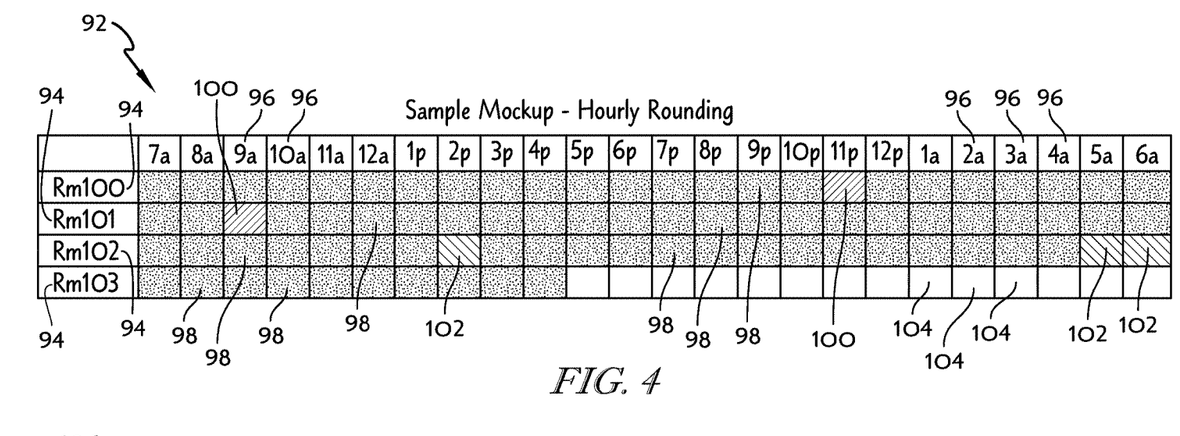
FIG. 4 is an example of a rounding compliance report showing cells of a table corresponding to one-hour time intervals and the cells being colored differently to indicate successful rounds, unsuccessful rounds, and suspended rounds.

Referring to FIG. 4, a compliance report includes a table 92 having rows 94 corresponding to room numbers of a wing or unit of a healthcare facility and having columns 96 corresponding to the rounding time intervals within which an assigned caregiver is expected to visit a patient associated with the respective room for a threshold amount of time in order to have a successful round. In the illustrative example of FIG. 4, the time interval for rounding is one hour for the entire 24-hour day. Green cells 98 in table 92 indicate a successful rounding event which means an assigned caregiver visited the patient room during the rounding time interval and remained in the patient room for at least the threshold amount of time. Yellow cells 100 in table 92 indicate that a caregiver visited the patient room but did not remain in the room for at least the threshold amount of time. Red cells 102 in table 92 indicate that a caregiver did not visit the patient room at any time during the rounding interval. White or blank cells 104 in table 92 indicate that no patient was assigned to the room during the rounding time interval.

Figure 5:
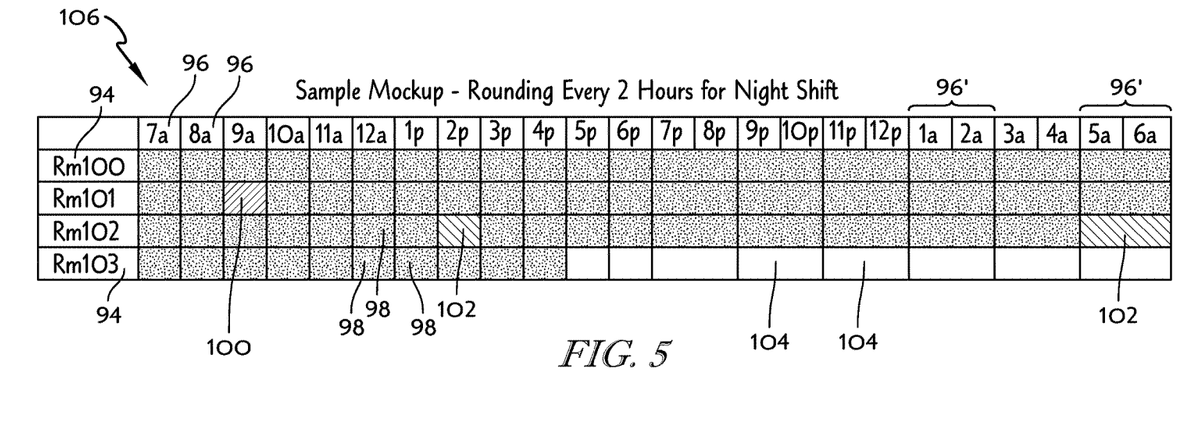
FIG. 5 is an example of a rounding compliance report, similar to FIG. 4, but showing some cells of the table corresponding to one-hour time intervals and other cells of the table corresponding to two-hour intervals.
Figure 6:
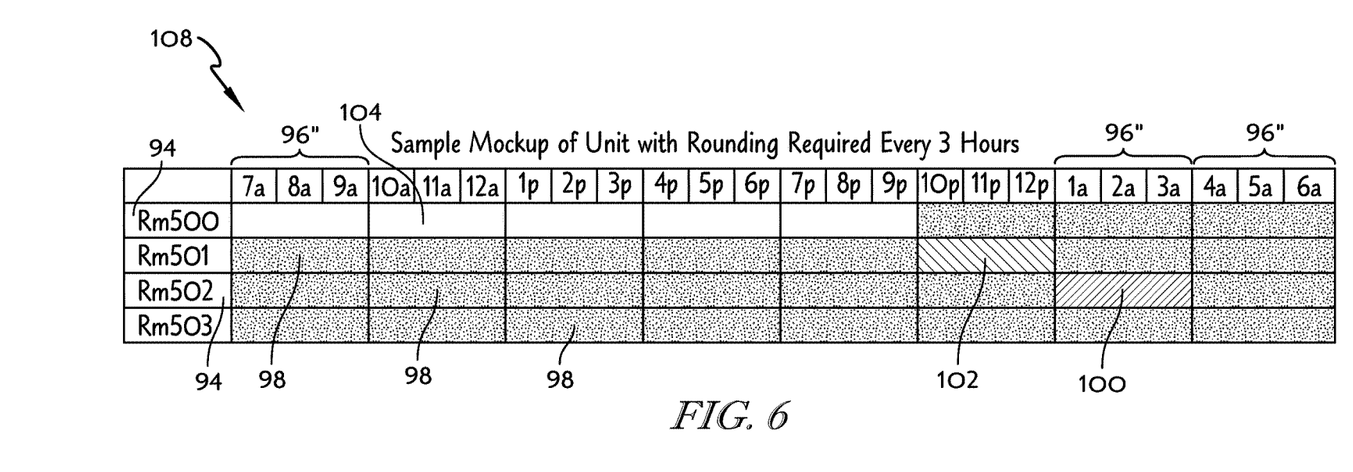
FIG. 6 is another example of a rounding compliance report, similar to FIGS. 4 and 5, but showing the cells of the table corresponding to three-hour time intervals.

Referring now to FIG. 5, a table 106 of an example of a compliance report is shown and is similar to table 92 except that the rounding time intervals during the night time hours are two hours in length as indicated in columns 96' of table 106. Other aspects that are the same in table 106 as in table 92 are denoted with like reference numbers. The color of the cells 98, 100, 102, 104 in table 106 indicate the same thing as in table 92. Referring now to FIG. 6, a table 108 of another example of a compliance report is shown and is similar to tables 92, 106 except that the rounding time intervals are three hours for the entire 24-hour day as indicated in columns 96" in table 108. Other aspects that are the same in table 108 as in tables 92, 106 are denoted with like reference numbers. The color of the cells 98, 100, 102, 104 in table 108 indicate the same thing as in tables 92, 106.

According to some embodiments of tables 92, 106, 108 other cell colors may be used to denote other types of events as determined by server 12. For example, if a rounding event was suspended using buttons 88 of window 84 as described above in connection with FIG. 3, then the cell corresponding to the time interval(s) of the suspension are colored gray in tables 92, 106, 108. As another example, the cells of table 92, 106, 108 are colored white with green, red or gray stripes if a rounding event happened in an empty room or a room in which no patient was assigned.

Figure 7:
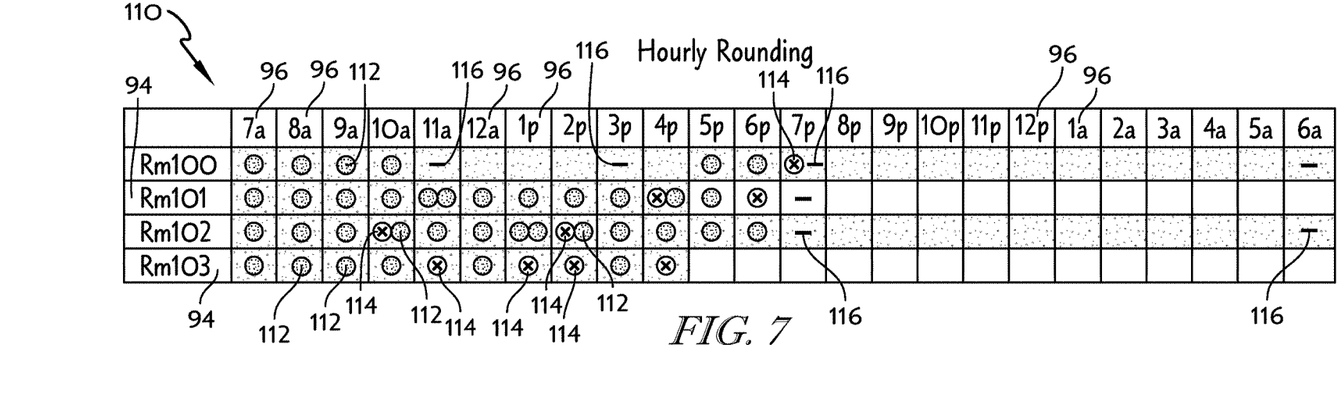
FIG. 7 is a further example of a rounding compliance report showing icons situated in the cells of the table to indicate successful, unsuccessful and suspended rounds.

Referring now to FIG. 7, a compliance report includes a table 110 having rows 94 corresponding to room numbers of a wing or unit of a healthcare facility and having columns 96 corresponding to one-hour time intervals similar to table 92 described above. However, in the illustrative example of FIG. 7, the time interval for rounding is still one hour but it resets to start counting the one hour rounding interval from the time the prior round was finished. For example, if a round is completed at 8:40 am, then the next round is due on or before 9:40 am. In table 110, the background of the cells are colored blue (indicated by light stippling in FIG. 7) if a patient is admitted to the room during the time intervals indicated in the columns 96 of the top row 94 of table 110 and the cells are colored white if no patient is admitted to the room during the relevant time interval.

Still referring to FIG. 7, a round green icon 112 in a cell of table 110 indicates a successful rounding event which means an assigned caregiver visited the patient room during the rounding time interval and remained in the patient room for at least the threshold amount of time. A round red icon 114, with an "x" in the middle in the illustrative example, is used in table 110 to indicate an unsuccessful round. A gray dash icon 116 is used to indicate the beginning and end of a suspension period of rounding. Due to the rounding time interval being reset when the prior round was complete, it is possible for some of the cells of table 112 to have two icons 112, 114, 116 in the cell as shown in various cells of FIG. 7. This is dictated by the manner in which the varying rounding time intervals overlap with the column 96 time intervals and the associated times at which rounding events associated with icons 112, 114, 116 happen to occur or not occur. The types of rounding compliance reports shown, for example, in FIGS. 4-6 are sometimes referred to as "clock reporting" and the types of rounding compliance reports shown, for example, in FIG. 7 are sometimes referred to as "event reporting."

Other compliance reports are contemplated by this disclosure. For example, a daily report that includes a single icon for each room of a wing or unit for each day indicates the compliance throughout the day. For example, on a given day, a single green icon or cell next to a room number indicates that all rounding events for the entire day were completed successfully; a single yellow icon or cell indicates that some, but not all rounding events were completed successfully, with less than 50% of the rounding events being unsuccessful; a single red icon or cell indicates that less than 50% of the rounding events were completed successfully, with more than 50% of the rounding events being unsuccessful; a single gray icon or cell to indicate that rounding was suspended for the entire day event though a patient was admitted to the associated room; and no icon or a white cell if no patient was admitted to the associated room. Thus, the daily report is a two column report with a left column listing the room numbers and the right column having the colored icons or cells as just described.

Figure 8:
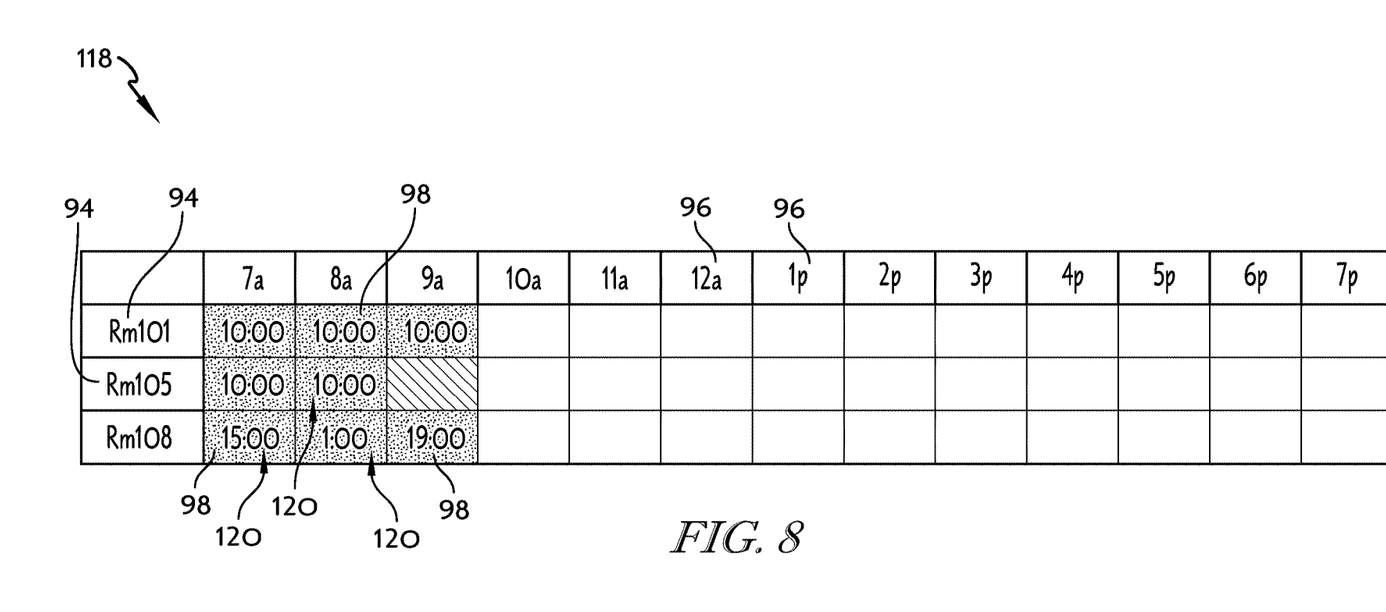
FIG. 8 is yet another example of a rounding compliance report showing, in the cells of the table corresponding to successful rounds, an amount of time that a caregiver was sensed to be in the patient room by the RTLS.

In some embodiments, the compliance reports generated by server 12 include the total amount of time that the caregiver was actually determined by server 12 to be in the associated room based on information received by server 12 from the RTLS 14. FIG. 8 shows an example of such a report having a table 118 with total times 120 that an assigned caregiver was located in the associated room displayed in an associated green cell 98. The total times 120 are displayed in yellow cells of table 118 in some embodiments, as well. By displaying the total time 120 in a yellow cell, it can be determined how close the caregiver's presence in the room was to the threshold amount of time that is needed to be considered a successful round. In some embodiments, red cells of table 118 include a time of zero (e.g. 00:00 for hours:minutes format or 00:00:00 for hours:minutes:seconds format) to further emphasize that an assigned caregiver did not spend any time in the patient's room during the associated time interval.

Figure 9:
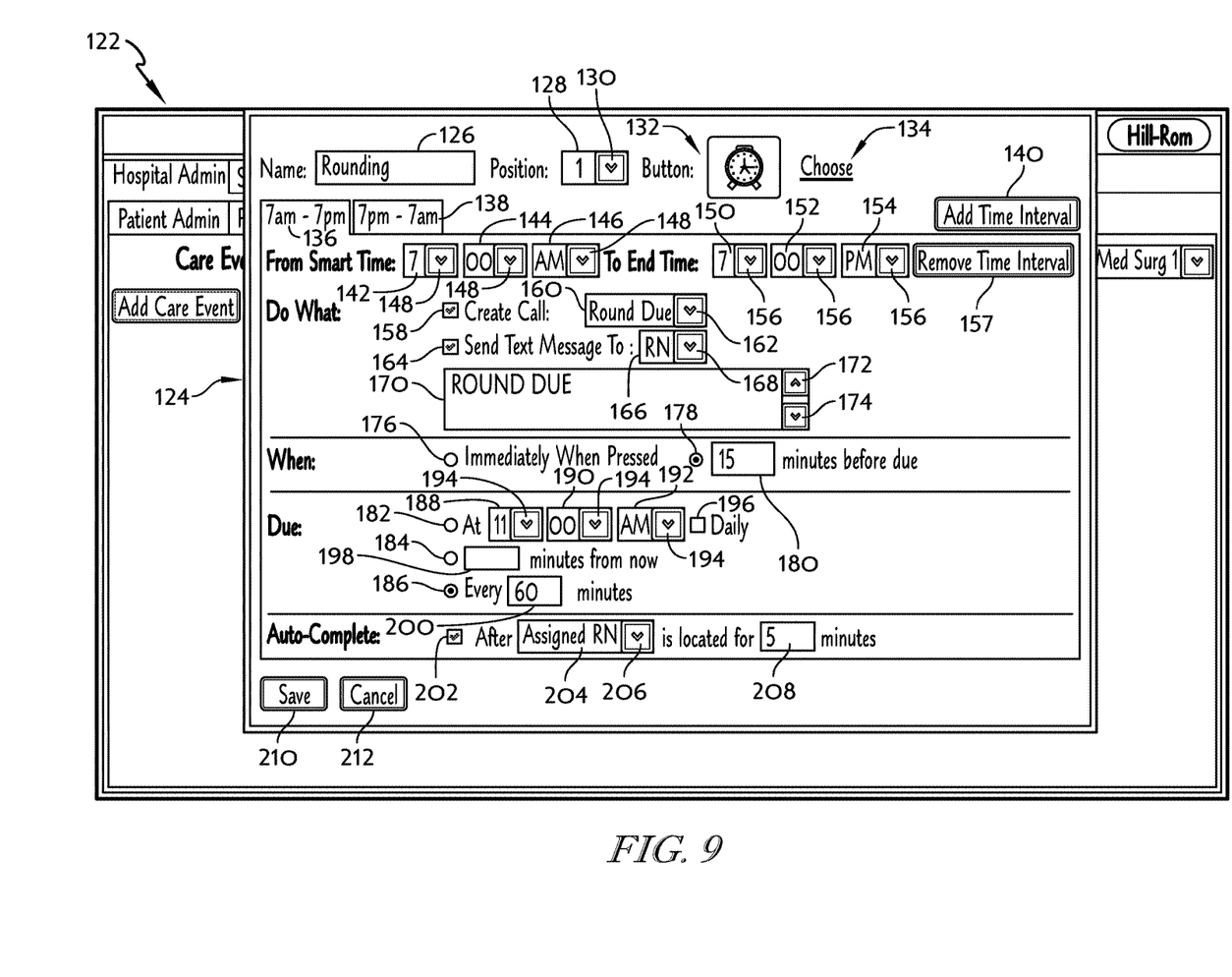
FIG. 9 is a screen shot of an administration screen that is used to add and remove time intervals, set up a time at which reminder messages are to be sent, and to set up the threshold period of time that a caregiver needs to be present in a patient's room before a round is considered to be successful.

Referring now to FIG. 9, an administration screen 122 is shown that is used to set up the rounding parameters of the rounding software of server 12. Thus, screen 122 appears on a monitor or touch screen display associated with server 12 in some embodiments. Screen 122 includes a pop-up window 124 which the various selections are made to set up rounding tasks and associated caregiver reminders. Window 124 includes a Name text box 126, a position box 128 with an associated drop down menu arrow 130, a button field 132, and a Choose button 134 adjacent to field 132.

Box 126 is used to enter the name of the icon of the associated task as it is to appear on screen 40 of graphical displays 26. In the illustrative example of FIG. 9, the word "Rounding" has been entered in box 126. Thus, a user selects box 126 such as with a mouse cursor, for example, and then uses a keyboard to type whatever word or words the user wishes for naming the associated task. Position box 128 is used to determine which position on screen 140 the task icon is to occupy. In FIG. 2, screen 40 has room for up to four icons on its top row. Thus, if drop down menu arrow 130 is selected a drop down menu having the numbers 1, 2, 3, 4 appears in window 124 and the user selects which numbered position on screen 40 (from left to right) the task icon is to occupy. Button field 132 shows an image of the icon that is to be used as the task button on screen 40. Selection of Choose button 134 causes the choices of the icons that are available for use on screen 40. So, in the illustrative example of FIG. 9, the user has chosen an alarm clock icon to be the icon used for Rounding at position 1 on screen 40.

Still referring to FIG. 9, window 124 has an Add Time Interval button 140 that is selected by the user to set up the time intervals and threshold times for the task associated with the icon in field 132. When button 140 is selected, the various data entry text boxes and radio buttons, etc. associated with a 7 am-7 pm tab 136 and a 7 pm-7 am tab 138 become active in window 124 for the user to make desired selections. Window 124 defaults to tab 136 in response to selection of button 140 as shown in FIG. 9. Tab 136 is associated with the day time parameters and tab 138 is associated with the night time parameters of the rounding software.

Under tab 136, window 124 includes an hours box 142, minutes box 144 and AM/PM box 146, each with a drop down menu arrow 148, for setting up a start time for the task associated with the icon of field 132. Selection of drop down menu arrows 148 associated with any of icons 142, 144, 146 results in a menu of hours (1 to 12), minutes (00 to 60) and AM/PM, respectively, appearing on screen 122 for the user to make subsequent start time selections. Under tab 136, window 124 also includes an hours box 150, minutes box 152 and AM/PM box 154, each with a drop down menu arrow 156, for setting up an end time for the task associated with the icon of field 132. Selection of drop down menu arrows 156 associated with any of icons 150, 152, 154 results in a menu of hours (1 to 12), minutes (00 to 60) and AM/PM, respectively, appearing on screen 122 for the user to make subsequent end time selections.

When tab 136 first becomes active via selection of button 140, boxes 142, 144, 146 initially default to 7:00 AM and boxes 150, 152, 154 initially default to 7:00 PM as the name of tab 136 implies. Similar defaults of 7:00 PM for boxes 142, 144, 146 and 7:00 AM for boxes 150, 152, 154 appear in connection with tab 138 as its name implies. However, the user is able to change the start and end times associated with each of tabs 136, 138 at the user's discretion. Window 124 haws a Remove Time Interval button 157 that is selected by the user to eliminate the task associated with the icon in field 132 from system 10. Thus, if the user does not want any rounding task to be set up from 7:00 AM to 7:00 PM, in the illustrative example, the user selects button 157 to accomplish that.

Beneath the start and end time boxes 142, 144, 146, 150, 152, 154 of window 124 is a create call check box 158 and a Call text box 160 with an associated drop down menu arrow 162. Box 158 is checked to set up a call alert in the software of server 12 if the task associated with the icon in field 132 is not completed in a timely manner. Text box 160 shows the type of call alert that is set up when box 158 is checked. If box 158 is unchecked, then there is no call alert established in system 10. Thus, in the illustrative example, a Rounding call alert is one of the types of alerts that is included in connection with call bell icon 74 and its associated number icon 78 as discussed above in connection with FIG. 2. Selection of drop down menu arrow 162 results in a menu of call type names being displayed in window 124 for subsequent selection by the user.

Beneath boxes 158, 160 of window 124 are a Send Text Message check box 164 and a To text box 166 with an associated drop down menu arrow 168. Box 164 is checked to command server 12 to send a reminder message to the particular portable wireless communication device 32, 34, 36 carried by an assigned caregiver. Box 166 indicates the type of assigned caregiver to which the message should be sent. In the illustrative example, the message is to be sent to the RN assigned to the patient of each room. The phone numbers or message addresses of devices 32, 34, 46 is stored in database 38 and correlated to the respective caregiver(s) assigned to each room in the unit or wing. Arrow 168 is selected to cause a display of the types of caregiver to whom the message may be sent. If box 164 is not checked, then no message is sent.

Beneath boxes 164, 166 of window 124 is a text box 170 in which the user types the particular message that is to be displayed on the caregiver's device 32, 34, 36. In the illustrative example, the message is "Round Due." This is the default message in box 170 and matches the selection made by the user for the call type in box 160. In some embodiments, server 12 appends the particular room number for which the round is due to the message typed in box 170, assuming the call type in box 160 is Round Due. Thus, an example of a reminder message seen on graphical displays 26 of devices 32, 34, 36 is "Round Due, Rm 6W-110." The user is able to type whatever message they wish in box 170 in lieu of the default message. For example, the user is able to select box 170 using a mouse cursor and then using an associated keyboard to compose the desired message. An up arrow 172 and a down arrow 174 is provided on the right side of box 170 for scrolling to see portions of the message that may not be seen in box 170 at any given time.

Beneath box 170 is an Immediately When Pressed radio button 176 that is toggled on and off via sequential selections of button 176, a second radio button 178 that is toggled on and off via sequential selections of button 178, and a minutes text box 180 that is adjacent radio button 178. The user enters the number of minutes before the end of the given time interval at which the task associated with the message in box 170 is to be sent to the caregiver designated in box 166. In the illustrative example, radio button 176 is not selected, radio button 178 is selected, and the number 15 is entered in box 180 so that a reminder message is sent to the RN 15 minutes before the end of the time interval associated with the rounding task. If radio button 176 is selected, then the message in box 170 is sent to the designated caregiver when the icon associated with field 132 is pressed on screen 40 of FIG. 2.

Beneath radio buttons 176, 178 and text box 180 are first, second, and third radio buttons 182, 184, 186 that are selected to indicate how often the task named in box 126 and having the icon shown in field 132 is due. Only one of buttons 182, 184, 186 can be selected at a time, such that selection of one of buttons 182, 184, 186 automatically deselects the other two of buttons 182, 184, 186. If button 182 is selected, then the associated task is due at a particular time as set forth by the user in hours, minutes, and AM/PM boxes 188, 190, 192, respectively, each of which has a drop down menu arrow 194. Boxes 188, 190, 192 and arrow 194 are used in a similar manner as boxes 142, 144, 146 and arrows 148 described above to establish a particular time. A Daily check box 196 is provided on window 124 adjacent to box 192 and the user is able to check this box if the associated task is due by the same time each day.

If button 184 is selected, then the associated task is due a number of minutes entered in a minutes box 198 from the time that the user finishes setting up the parameters of the associated task using window 124. If button 186 is selected, as is the case in the illustrative example of FIG. 9, then the associated task is a recurring task that is due within interval times having the number of minutes entered in a minutes box 200 by the user. In the illustrative example, the rounding task indicated in box 126 and associated with the icon in field 132 is due every 60 minutes from 7:00 AM (entered in boxes 142, 144, 146) until 7:00 PM (entered in boxes 150, 152, 154) because 60 has been entered in the minutes box 200 by the user.

Beneath button 186 and box 200 is an Auto-Complete check box 202 which is selected by the user if the associated task is to be considered complete automatically by server 12 in connection with a designated caregiver being sensed by RTLS 14 as being present within the patient room associated with the task for a threshold period of time. A caregiver text box 204 and accompanying drop down menu arrow 206 is provided in window 124 adjacent to check box 202 for entry of the designated caregiver type. In the illustrative example, "Assigned RN" appears in box 204. Selection of arrow 206 causes a drop down menu of other caregiver types to appear on window 124 for subsequent selection by the user. A threshold time box 208 is provided in window 124 next to box 204 and used to enter the number of minutes of the threshold time. In the illustrative example, 5 is entered in box 208. Thus, in the illustrative example, server 12 automatically determines a successful rounding event to have occurred if an assigned RN is located in the room associated with the task for 5 minutes. The user can enter in box 208 whatever time, in minutes, the user wishes within minimum and maximum amounts (e.g., 1 minute to 30 minutes).

In the lower left corner of window 124, a Save button 210 and a Cancel button 212 are provided. Selection of Save button 210 by the user results in all of the parameters entered by the user in window 124 in the various boxes, fields, buttons, etc. to be saved by server 12 in database 38. Server 124 then operates according to those saved parameters and commands graphical displays 26 to display the associated information, such as icons, messages, and so forth, as described above in this disclosure, based in part on the parameter selections made in window 124. If the user selects Cancel button 212, then the selections made by the user in window 124 are canceled, window 124 replaces the canceled entries with prior entries, if any, that were shown in window 124 when it was first opened by the user, and window 124 shuts down. It will be appreciated that other administration functions, such as designating assigned caregivers to the various rooms are performed on other administration screens as is well-known in the art.

In some embodiments, some or all of room stations 30 do not include graphical displays 26. Such alternative room stations are sometimes referred to as standard room stations (SRS's) or standard audio stations (SAS's). See U.S. Patent Application Publication No. 2009/0212956 A1, which is already incorporated by reference herein, for a discussion of these types of room stations. In such embodiments, RTLS 14 is still able to track the whereabouts of caregivers, server 12 is still able to determine compliance with rounding protocols, and reminders are still able to be sent to devices 32, 34, 36 carried by caregivers. Furthermore, caregivers are able to suspend rounding for any given patient room using either the master nurse station computer, an input device associated with server 12, or using inputs on devices 32, 34, 36.

Although certain illustrative embodiments have been described in detail above, many embodiments, variations and modifications are possible that are still within the scope and spirit of this disclosure as described herein and as defined in the following claims.

The invention claimed is:

1. An information technology system for a healthcare facility having a real time locating system (RTLS) for tracking locations of a plurality of caregivers within the healthcare facility, the information technology system comprising
at least one computer device to keep track of rounding for a plurality of caregivers and to determine whether the caregivers successfully complete their rounds in a timely manner for their assigned patients, a successful round being defined as one in which a caregiver visits an assigned patient within a rounding interval and remains in the patient's room for an in-room threshold period of time, and
a plurality of graphical displays in communication with the at least one computer device, each graphical display being operable to display a list of patients for whom rounds are due and to display reminder messages to the plurality of caregivers relating to rounding, wherein the at least one computer device is used to administer rounding parameters for each of the plurality of caregivers, wherein different types of caregivers have different rounding parameters, wherein the rounding parameters include the in-room threshold period of time such that different types of caregivers have different in-room threshold periods of time for determining successful completion of their rounds.

2. The system of claim 1, wherein the at least one computer device determines automatically that the caregivers successfully complete each of their rounds based on information received from the RTLS indicating that the caregivers are located within the patient rooms of the patients within the rounding intervals and for the in-room threshold periods of time.

3. The system of claim 1, wherein the at least one computer device is included as part of a nurse call system and wherein the plurality of graphical displays comprise graphical room stations of the nurse call system that are mounted in respective patient rooms.

4. The system of claim 1, wherein the rounding parameters further include the rounding interval.

5. The system of claim 1, wherein each graphical display of the plurality of graphical displays is useable by each caregiver to indicate to the at least one computer device that the round is complete.

6. The system of claim 1, wherein each graphical display of the plurality of graphical displays is useable by each caregiver to indicate to the at least one computer device that a task, other than rounding, is complete.

7. The system of claim 1, wherein each graphical display of the plurality of graphical displays is useable by each caregiver to re-prioritize tasks assigned to the caregiver.

8. The system of claim 1, wherein each graphical display of the plurality of graphical displays is useable by each caregiver to cancel or suspend an assigned task.

9. The system of claim 1, wherein each graphical display of the plurality of graphical displays also is operable to show at least one timer relating to rounding or at least one timer related to a task other than rounding or both.

10. The system of claim 1, wherein at least some graphical displays of the plurality of graphical displays are included in a tablet computer, a mobile telephone, or a smart phone.

11. The system of claim 1, wherein the plurality of graphical displays are operable to show at least one icon that is selected to place a call to a staff member and wherein the staff member includes at least one of a registered nurse (RN), a certified nurse assistant (CNA), a transporter, and an environmental services person.

12. The system of claim 1, wherein the at least one computer device is operable to change the rounding intervals.

13. The system of claim 1, wherein the at least one computer device is operable to select an amount of time prior to expiration of the rounding intervals at which rounding reminder messages are sent to the plurality of graphical displays.

14. The system of claim 1, wherein the at least one computer device is operable to change the in-room threshold periods of time.

15. The system of claim 1, wherein the first computer device is operable to generate a rounding compliance report comprising a table having blocks that indicate a successful round within the rounding interval, an unsuccessful round, and a suspended round.

16. The system of claim 15, wherein an amount of time that the caregiver was located in each room is shown in each block of the table for each successful round.

17. The system of claim 15, wherein the blocks are colored a first color to indicate successful rounds, the blocks are colored a second color to indicate unsuccessful rounds, and the blocks are colored a third color to indicate suspended rounds.

18. The system of claim 15, wherein first icons are shown in the blocks to indicate successful rounds, second icons are shown in the blocks to indicate unsuccessful rounds, and third icons are shown in the blocks to indicate suspended rounds.

19. The system of claim 1, wherein the in-room threshold periods of time vary based on a time of day.

20. The system of claim 1, wherein the rounding interval varies based on a time of day.

* * * * *